United States Patent [19]

Podraza et al.

[11] Patent Number: 4,872,918
[45] Date of Patent: Oct. 10, 1989

[54] HETEROCYCLIC ESTERS AND SMOKING COMPOSITIONS CONTAINING A HETEROCYCLIC ESTER FLAVORANT-RELEASE ADDITIVE

[75] Inventors: Kenneth F. Podraza; Yoram Houminer, both of Richmond, Va.

[73] Assignee: Philip Morris Incorporated, New York, N.Y.

[21] Appl. No.: 861,945

[22] Filed: May 12, 1986

[51] Int. Cl.$^4$ .......................... A24B 3/12; A24B 15/36
[52] U.S. Cl. .................................... 131/277; 131/278; 131/279
[58] Field of Search ........................ 131/277, 278, 279

Primary Examiner—V. Millin

[57] ABSTRACT

This invention provides novel heterocyclic ester compounds. This invention further provides smoking compositions which contain an invention heterocyclic ester as a flavorant-release additive, as illustrated by the following structure:

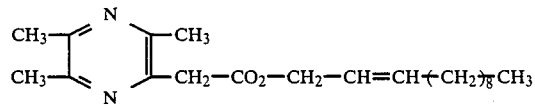

Under normal cigarette smoking conditions, tetramethylpyrazine and an olefin are released as pyrolysis products, and they enhance the flavor and aroma of the mainstream and sidestream smoke.

24 Claims, No Drawings

HETEROCYCLIC ESTERS AND SMOKING COMPOSITIONS CONTAINING A HETEROCYCLIC ESTER FLAVORANT-RELEASE ADDITIVE

BACKGROUND OF THE INVENTION

It has been established that alkylpyrazines are natural components of tobacco smoke, and that they most probably are important contributors to tobacco smoke flavor [A. Baggett et al J. Chromatog. 97, 79 (1974)]. Further, it has been disclosed in the patent literature that addition of alkylpyrazines to tobacco results in an improvement in the flavor of smoking compositions as perceived by a test panel.

U.S. Pat. No. 3,402,051 describes a process for imparting a popcorn-like flavor and aroma to tobacco and foodstuffs by the incorporation of a 2-acetylpyrazine derivative therein.

Other patents which disclose the addition of various pyrazine compounds to tobacco and foodstuffs as a means of providing flavor or flavor enhancement include U.S. Pat. Nos. 3,684,809; 3,705,158; 3,754,934; 3,764,349; 3,767,426; and 3,881,025.

U.S. Pat. No. 3,914,227 discloses pyridyl and pyrazyl ketones and their use in altering the pyrazyl ketones and their use in altering the organoleptic properties of tobacco and foodstuffs, and U.S. Pat. No. 4,166,869 discloses acylpyrimidines useful as flavorants for the same type of applications.

Alkylpyridines have also been found to be useful tobacco additives. As an example, U.S. Pat. No. 3,625,224 describes the use of methylpyridines, ethylpyridines and various dialkylpyridines as tobacco additives. U.S. Pat. No. 3,381,691 discloses 2-methyl-5-isopropylpyridine as a tobacco additive.

It is characteristic of pyridine, pyrazine, pyrimidine and other heterocyclic derivatives employed as tobacco flavorants in the prior art, as illustrated by the above described technical literature, that the respective heterocyclic derivatives have the disadvantage of both high volatility and low odor threshold. Both of these properties significantly restrict the extent that these heterocyclic derivatives can be utilized as flavorants in tobacco compositions. A quantity of a pyrazine or pyridine derivative in a tobacco composition sufficient to have a noticeable effect in low delivery cigarettes causes a marked pack aroma.

U.S. Pat. No. 4,036,237 endeavors to overcome some of the disadvantages of the above-described flavorant technology. The said patent provides for the incorporation in smoking compositions of a flavorant compound which imparts cherry-like or fruity flavor to the smoke thereof, which flavorant compound is not lost during the manufacture and storage of the flavored smoking composition, and which is readily released when the smoking composition is burned. Illustrative of a U.S. Pat. No. 4,036,237 flavorant compound is ethyl 2,2-dimethyl-3-hydroxy-3-phenylpropionate.

U.S. Pat. No. 4,259,969 describes smoking composition flavorant-release additives such as 2,3-dihydroxy-2,3-dimethyl-1,4-bis(3,5,6-trimethyl-2-pyrazinyl) butane. Under smoking conditions there are released substituted-pyrazine pyrolysis products which enhance the flavor of the mainstream smoke and improve the aroma of the sidestream smoke.

U.S. Pat. No. 4,312,368 and related U.S. Pat. No. 4,479,003 describe heterocyclic-hydroxy-substituted alkanoate flavorant additives such as ethyl 2-(2-butyl)-3-hydroxy-3-methyl-3-(3-pyridyl)propionate:

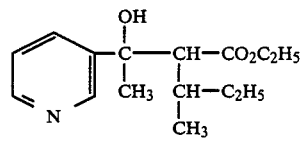

Under normal smoking conditions the flavorant additive pyrolyzes into components which contribute enhanced flavor and aroma to the smoke streams.

There is continuing research effort to develop improved smoking compositions which contain a new and efficient low volatility flavorant-release additive, and which generate mainstream smoke with flavorant-enhanced taste and character under smoking conditions.

Accordingly, it is an object of this invention to provide smoking compositions having incorporated therein a flavorant component which is characterized by lack of mobility and/or volatility at ambient temperature.

It is another object of this invention to provide smoking compositions having incorporated therein a flavorant-release additive which under normal smoking conditions yields pyrolysis constituents which impart improved flavor to mainstream smoke and improved aroma to sidestream smoke.

It is a further object of this invention to provide novel ester compounds of low volatility which are adapted to be incorporated into cigarette fillers, and which under normal smoking conditions release volatile heteroaromatic and other flavorant constituents into cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001-5 weight percent, based on the total weight of filler, of a novel flavorant-release additive corresponding to the formula:

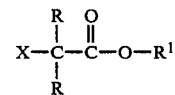

where X is a heteroaromatic substituent containing between about 3-20 carbon atoms; R is hydrogen or an alkyl radical containing between about 1-4 carbon atoms; and $R^1$ is an allylic aliphatic radical containing between about 10-25 carbon atoms.

Illustrative of the X substituent are heteroaromatic structures such as substituted and unsubstituted pyridyl, pyrazyl, thiazyl, furyl, and thienyl monovalent radicals.

Illustrative of the R substituent are hydrogen, methyl, ethyl, propyl, butyl, isobutyl and 2-butyl radicals.

Illustrative of the $R^1$ substituent are aliphatic structures such as straight chain and branched chain 2-alkenyl radicals which contain between about 10-25 carbon atoms.

Illustrative of $R^1$ substituents are 2-decenyl, 2-dodecenyl, 3-ethyl-2-decenyl, 3,7-dimethyl-2,6-octadien-1-yl, 2-hexadecenyl, 2-eicosenyl, 2-cyclopentyl-2-eicosenyl, and the like.

In another embodiment, this invention provides a heterocyclic ester composition corresponding to the formula:

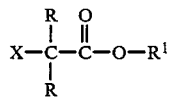

where X is a heteroaromatic substituent containing between about 3-20 carbon atoms; R is hydrogen or an alkyl radical containing between about 1-4 carbon atoms; and $R^1$ is an allylic aliphatic radical containing between about 10-25 carbon atoms.

In the above illustrated heterocyclic ester composition, a preferred X substituent is a heteroaromatic structure corresponding to one of the formulae:

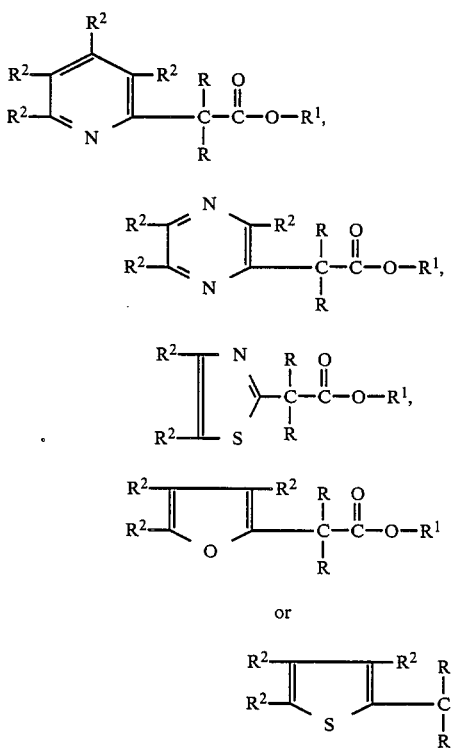

or where R is hydrogen or an alkyl radical containing between about 1-4 carbon atoms, $R^2$ is hydrogen or an alkyl or alkoxyl radical containing between about 1-4 carbon atoms, and $R^1$ is a 2-alkenyl radical containing between about 10-25 carbon atoms.

Illustrative of $R^2$ substituents in the above formulae are hydrogen, methyl, ethyl, propyl, butyl, isobutyl, 2-butyl, methoxy, ethoxyl, propoxyl, butoxy, and the like. R and $R^1$ are as previously defined and illustrated.

An invention heterocyclic ester compound as described above, when incorporated in a smoking composition, is a low volatility additive which under normal smoking conditions pyrolyzes into volatile constituents which enhance the flavor and aroma of low delivery cigarette smoke.

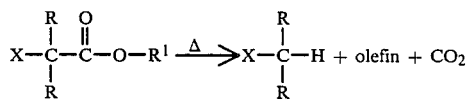

The present invention heterocyclic ester flavorant-release additives are stable and odorless compounds at ambient temperature. In addition, the heterocyclic esters decompose at a relatively low pyrolysis temperature (e.g., 150°-300° C.) to release a high yield of desirable flavor-enhancing heteroaromatic and olefin components in mainstream smoke.

PREPARATION OF HETEROCYCLIC ESTERS

A general procedure for the preparation of present invention heterocyclic ester flavorant-release compounds involves the reaction of a selected heterocyclic acetate salt with an allylic alcohol in a solvent medium:

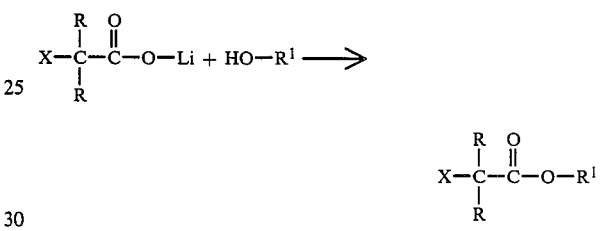

where X, R and $R^1$ are as previously defined.

PREPARATION OF SMOKING COMPOSITIONS

In a further embodiment, this invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001-5 weight percent, based on composition weight, of a flavorant-release additive corresponding to the formula:

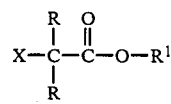

where X is a heteroaromatic substituent containing between about 3-20 carbon atoms; R is hydrogen or an alkyl radical containing between about 1-4 carbon atoms; and $R^1$ is an allylic aliphatic radical containing between about 10-25 carbon atoms.

The invention flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein; incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

The following Examples are further illustrative of the present invention. The specific ingredients and processing parameters are presented as being typical, and various modifications can be derived in view of the foregoing disclosure within the scope of the invention.

EXAMPLE I 3,7-Dimethyl-2,6-octadien-1-yl 3,5,6-trimethyl-2-pyrazineacetate

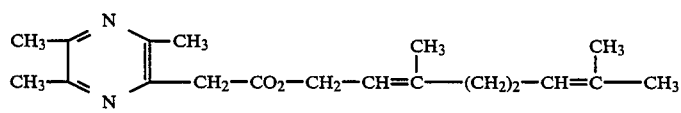

To a solution of 3,5,6-trimethyl-2-pyrazineacetic acid lithium salt (2.0 g, 10.8 mmoles) in 1,2-dimethoxyethane (50 ml) at 0° C. are added sequentially pyridine (1.7 g, 21.6 mmoles), phenyl dichlorophosphate (3.42 g, 16.2 mmoles), and 3,7-dimethyl-2,6-octadien-1-ol (4.6 g, 21.6 mmoles). The resulting mixture is stirred at room temperature under an atmosphere of nitrogen for approximately 18 hours.

The mixture is poured into ice-cold water and extracted with chloroform. The combined chloroform extracts are washed with aqueous saturated ammonium chloride, then with water, and dried over anhydrous magnesium sulfate. Evaporation of the chloroform solvent under reduced pressure yields a residual liquid. The liquid is purified by preparative thin layer chromatography on silica gel eluted with chloroform then ethyl acetate. A 1.2 g quantity of purified oil product is obtained.

NMR and IR confirm the structure of the title compound.

Anal. calc. for $C_{19}H_{28}N_2O_2$: C,72.12; H,8.92; N,8.85
Found: C,72.27; H,8.96; N,8.68

If 2-furanacetic acid lithium salt is employed as the acetate starting material, then 3,7-dimethyl-2,6-octadien-1-yl 2-furanacetate product is obtained.

EXAMPLE II 3,7,11-Trimethyl-1,6,10-dodecatrien-3-yl 3,5,6-trimethyl-2-pyrazineacetate

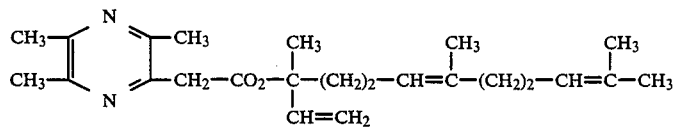

The reaction between 3,5,6-trimethyl-2-pyrazineacetic acid lithium salt and 3,7,11-trimethyl-1,6,10-dodecatrien-3-ol is conducted on a 5.4 mmole scale employing the conditions described in Example I. The residual crude liquid product is purified by high pressure liquid chromatography on a silica gel column with 40% ethyl acetate/hexane as the eluent. A 200 mg yield of pure oil product is obtained.

NMR and IR confirm the structure of the title compound.

Anal. calc. for C: $C_{24}H_{36}N_2O_2$: C,74.96; H,9.44; N,7.28
Found: C,74.83; H,9.40; N,7.12

EXAMPLE III 3,7,11-Trimethyl-1,6,10-dodecatrien-3-yl 2-(2-pyrazine)propionate

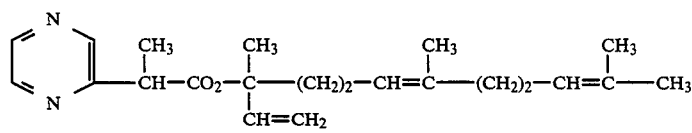

The reaction between 2-(2-pyrazine)propionic acid lithium salt and 3,7,11-trimethyl-1,6,10-dodecatrien-3-ol is conducted on a 12.7 mmole scale employing the same conditions as described in Example I. The liquid is purified by high pressure liquid chromatography on a silica gel column with 35% ethyl acetate/hexane as the eluent. A 150 mg yield of pure oil product is obtained.

NMR and IR confirm the structure of the title compound.

Anal. calc. for $C_{22}H_{32}N_2O_2$: C,73.91; H,9.30; N,7.83
Found: C,73.71; H,9.13; N,7.65

If 2-thiopheneacetic acid lithium salt is employed as the acetate starting material, then 3,7,11-trimethyl-1,6,10-dodecatrien-3-yl 2-thiopheneacetate is obtained.

EXAMPLE IV 3,7,11-Trimethyl-1,6,10-dodecatrien-3-yl 2-pyridineacetate

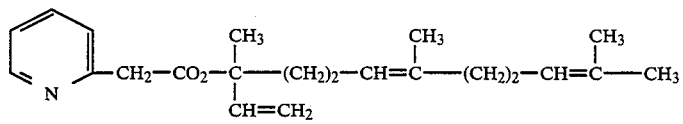

The reaction between 2-pyridineacetic acid lithium salt and 3,7,11-trimethyl-1,6,10-dodecatrien-3-ol is conducted on a 11.5 mmole scale employing the same conditions as described in Example I. The liquid was purified by preparative thin layer chromatography on silica gel using 10% ethyl acetate/hexane as the eluent. A 2.0 g yield of pure oil product is obtained.

NMR and IR confirm the structure of the title compound.

Anal. calc. for $C_{22}H_{31}NO_2$: C,77.38; H,9.15; N,4.10
Found : C,77.12; H,8.93; N,4.01

EXAMPLE V 3,7,11-Trimethyl-1,6,10-dodecatrien-3-yl 4,5-dimethyl-2-thiazoleacetate

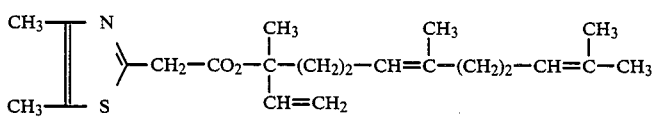

The reaction between 4,5-dimethyl-2-thiazoleacetic acid lithium salt and 3,7,11-trimethyl-1,6,10-dodecatrien-3-ol is conducted on an 8.5 mmole scale employing the same conditions as described in Example I. The liquid was purified by preparative thin layer chromatography on silica gel using from 2% to 10% ethyl acetate/hexane as the eluent. A 500 mg yield of pure oil product is obtained.

NMR and IR confirm the structure of the title compound.

Anal. calc. for $C_{22}H_{33}NO_2S$: C,70.36; H,8.86; N,3.73; S,8.54
Found : C,70.15; H,8.67; N,3.54; S,8.62

EXAMPLE VI

3-Buten-2-yl 3,5,6-trimethyl-2-pyrazineacetate

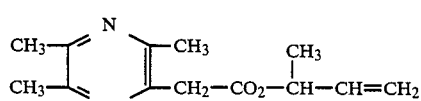

The reaction between 3,5,6-trimethyl-2-pyrazineacetic acid lithium salt and 3-buten-2-ol is conducted on a 5.4 mmole scale using the same conditions as described in Example I. The liquid was purified by high pressure liquid chromatography on a silica gel column with 50% ethyl acetate/hexane as the eluent. A 250 mg yield of pure oil product is obtained.

NMR and IR confirm the structure of the title compound.

Anal. calc. for $C_{13}H_{18}N_2O_2$: C,66.65; H,7.74; N, 11.95
Found: C,66.43; H,7.90; N,11.77

EXAMPLE VII

Decyl 3,5,6-trimethyl-2-pyrazineacetate

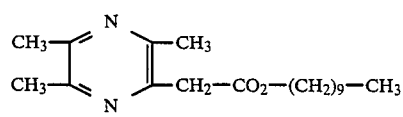

1-Chlorodecane (16.05 g, 90.8 mmoles) is added to a solution of 3,5,6-trimethyl-2-pyrazineacetic acid lithium salt (3.0 g, 22.7 mmoles) in dimethylformamide (50 ml) and hexamethylphosphoramide (100 ml) at 0° C. The resulting mixture is stirred at room temperature under an atmosphere of nitrogen for approximately 18 hours.

The mixture is poured into ice-cold water and extracted with ether. The combined ether extracts are washed with water and dried over anhydrous sodium sulfate. Evaporation of the solvent under reduced pressure yields 12.0 g of a residual liquid product. A 1.5 g sample of the liquid is purified by preparative thin layer chromatography on silica gel eluted with chloroform and then ethyl acetate. A 300 mg yield pure oil product is obtained.

NMR and IR confirm the structure of the title compound.

Anal. calc. for $C_{19}H_{32}N_2O_2$: C,71.21; H,10.06; N,8.74
Found: C,71.43; H,9.98 N,8.56

EXAMPLE VIII

Hexadecyl 3,5,6-trimethyl-2-pyrazineacetate

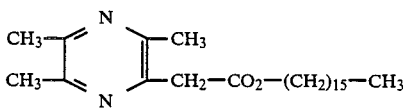

The reaction between 3,5,6-trimethyl-2-pyrazineacetic acid lithium salt and 1-chlorohexadecane is conducted on a 22.7 mmole scale using the conditions described in Example VII. A 1.5 g sample of the solid material is purified by preparative thin layer chromatography on silica gel eluted with methylene chloride then ethyl acetate. A 500 mg yield of pure product is obtained as a solid, m.p. 56°–57° C.

NMR and IR confirm the structure of the title compound.

Anal. calc. for $C_{25}H_{44}N_2O_2$: C,74.21; H,10.92, N,6.92
Found: C,74.14; H,10.83; N,6.78

EXAMPLE IX

Methyl 3,5,6-trimethyl-2-pyrazineacetate

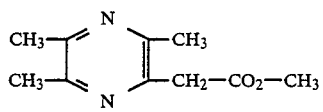

3,5,6-Trimethyl-2-pyrazineacetic acid lithium salt (10.0 g, 75.7 mmoles) is added to methanol (162 g) at 0° C. Hydrogen chloride gas is bubbled through the solution for approximately 30 minutes. The resulting solution is allowed to stand at room temperature for 4 days.

Evaporation of the solvent under reduced pressure yields residual product. The product is chilled to 0° C., and ice-cold chloroform and anhydrous potassium carbonate are added and stirred vigorously. Aqueous saturated potassium carbonate is added until the mixture is neutral. The mixture is filtered and dried over anhydrous magnesium sulfate.

Evaporation of the solvent under reduced pressure yield a residual liquid product which is purified by vacuum distillation, b.p. 73°–75° C. 0.025 mm Hg. The liquid product solidifies on standing.

NMR and IR confirm the structure of the title compound.

EXAMPLE X

This Example illustrates the reactivities of the Examples I-IX compounds under pyrolysis conditions.

A 10–50 mg sample of each of the Examples I-IX title compounds are pyrolyzed in a tube at 250° C. for 10 minutes. The yield of the pyrolysis released heteroaromatic flavorant moiety in each case is determined by HPLC. The pyrolysis results are summarized below.

| COMPOUND | FLAVORANT | YIELD % |
| --- | --- | --- |
| I | Tetramethylpyrazine | 10 |
| II | Tetramethylpyrazine | 50 |
| III | Ethyl pyrazine | 75 |
| IV | 2-picoline | 40 |
| V | 2,4,5-Trimethyl thiazole | 45 |
| VI | Tetramethylpyrazine | 0 |
| VII | Tetramethylpyrazine | 0 |
| VIII | Tetramethylpyrazine | 0 |
| IX | Tetramethylpyrazine | 0 |

The pyrolysis data indicate that a starting ester compound which does not contain an allylic alcohol function, or which contains a short chain allylic alcohol substituent, does not pyrolyze and release a heteroaromatic flavorant as a volatile component of the gaseous effluent.

What is claimed is:

1. A smoking composition comprising an admixture of (1) combustible filler selected from natural tobacco, reconstituted tobacco and tobacco substitutes, and (2) between about 0.0001–5 weight percent, based on the total weight of filler, of a flavorant-release additive corresponding to the formula:

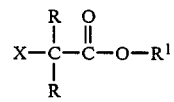

where X is a heteroaromatic substituent containing between about 3–20 carbon atoms; R is hydrogen or an alkyl radical containing between about 1–4 carbon atoms; and $R^1$ is an allylic aliphatic radical containing between about 10–25 carbon atoms.

2. A smoking composition in accordance with claim 1 wherein the heteroaromatic substituent comprises a 2-pyridyl radical.

3. A smoking composition in accordance with claim 1 wherein the heteroaromatic substituent comprises a 2-pyrazyl radical.

4. A smoking composition in accordance with claim 1 wherein the heteroaromatic substituent comprises a 2-thiazyl radical.

5. A smoking composition in accordance with claim 1 wherein the heteroaromatic substituent comprises a 2-furyl radical.

6. A smoking composition in accordance with claim 1 wherein the heteroaromatic substituent comprises a 2-thienyl radical.

7. A smoking composition in accordance with claim 1 wherein the allylic aliphatic radical comprises a 2-alkenyl radical containing between about 10–25 carbon atoms.

8. A smoking composition in accordance with claim 1 wherein the flavorant-release additive is 3,7-dimethyl-2,6-octadien-1-yl 3,5,6-trimethyl-2-pyrazineacetate.

9. A smoking composition in accordance with claim 1 wherein the flavorant-release additive is 3,7,11-trimethyl-1,6,10-dodecatrien-3-yl 3,5,6-trimethyl-2-pyrazineacetate.

10. A smoking composition in accordance with claim 1 wherein the flavorant-release additive is 3,7,11-trimethyl-1,6,10-dodecatrien-3-yl 2-(2-pyrazine)propionate.

11. A smoking composition in accordance with claim 1 wherein the flavorant-release additive is 3,7,11-trimethyl-1,6,10-dodecatrien-3-yl 2-pyridineacetate.

12. A smoking composition in accordance with claim 1 wherein the flavorant-release additive is 3,7,11-trimethyl-1,6,10-dodecatrien-3-yl 4,5-dimethyl-2-thiazoleacetate.

13. A method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a flavorant-release additive corresponding to the formula:

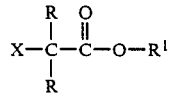

where X is a heteroaromatic substituent containing between about 3–20 carbon atoms; R is hydrogen or an alkyl radical containing between about 1–4 carbon atoms; and $R^1$ is an allylic aliphatic radical containing between about 10-25 carbon atoms.

14. A heterocyclic ester composition corresponding to the formula:

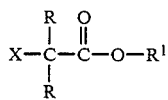

where X is a heteroaromatic substituent containing between about 3-20 carbon atoms; R is hydrogen or an alkyl radical containing between about 1-4 carbon atoms; and $R^1$ is an allylic aliphatic radical containing between about 10-25 carbon atoms.

15. A heterocyclic ester composition corresponding to the formula:

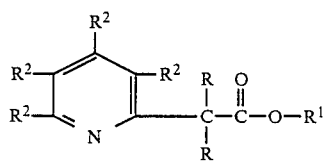

where R is hydrogen or an alkyl radical containing between about 1-4 carbon atoms, $R^2$ is hydrogen or an alkyl or alkoxyl radical containing between about 1-4 atoms, and $R^1$ is a 2-alkenyl radical containing between about 10-25 carbon atoms.

16. A heterocyclic ester composition corresponding to the formula:

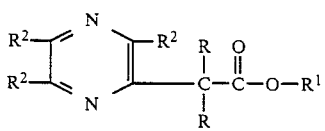

where R is hydrogen or an alkyl radical containing between about 1-4 carbon atoms, $R^2$ is hydrogen or an alkyl or alkoxyl radical containing between about 1-4 atoms, and $R^1$ is a 2-alkenyl radical containing between about 10-25 carbon atoms.

17. A heterocyclic ester composition corresponding to the formula:

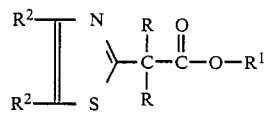

where R is hydrogen or an alkyl radical containing between about 1-4 carbon atoms, $R^2$ is hydrogen or an alkyl or alkoxyl radical containing between about 1-4 atoms, and $R^1$ is a 2-alkenyl radical containing between about 10-25 carbon atoms.

18. A heterocyclic ester composition corresponding to the formula:

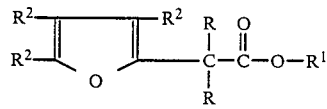

where R is hydrogen or an alkyl radical containing between about 1-4 carbon atoms, $R^2$ is hydrogen or an alkyl or alkoxyl radical containing between about 1-4 atoms, and $R^1$ is a 2-alkenyl radical containing between about 10-25 carbon atoms.

19. A heterocyclic ester composition corresponding to the formula:

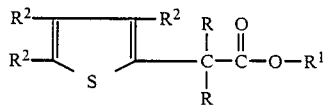

where R is hydrogen or an alkyl radical containing between about 1-4 carbon atoms, $R^2$ is hydrogen or an alkyl or alkoxyl radical containing between about 1-4 atoms, and $R^1$ is a 2-alkenyl radical containing between about 10-25 carbon atoms.

20. 3,7-Dimethyl-2,6-octadien-1-yl 3,5,6-trimethyl-2-pyrazineacetate.

21. 3,7,11-Trimethyl-1,6,10-dodecatrien-3-yl 3,5,6-trimethyl-2-pyrazineacetate.

22. 3,7,11-Trimethyl-1,6,10-dodecatrien-3-yl 2-(2-pyrazine)propionate.

23. 3,7,11-Trimethyl-1,6,10-dodecatrien-3-yl 2-pyridineacetate.

24. 3,7,11-Trimethyl-1,6,10-dodecatrien-3-yl 4,5-dimethyl-2-thiazoleacetate.

* * * * *